US010215692B2

(12) United States Patent
Tao et al.

(10) Patent No.: US 10,215,692 B2
(45) Date of Patent: Feb. 26, 2019

(54) OPTICAL WAVEGUIDE STRUCTURE AND OPTICAL GAS SENSOR, AND METHODS OF FABRICATION THEREOF

(71) Applicant: Agency for Science, Technology and Research, Singapore (SG)

(72) Inventors: Jifang Tao, Singapore (SG); Hong Cai, Singapore (SG); Alex Yuandong Gu, Singapore (SG); Hyun Kee Chang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/519,011

(22) PCT Filed: Oct. 16, 2015

(86) PCT No.: PCT/SG2015/050394
§ 371 (c)(1),
(2) Date: Apr. 13, 2017

(87) PCT Pub. No.: WO2016/060619
PCT Pub. Date: Apr. 21, 2016

(65) Prior Publication Data
US 2017/0227456 A1 Aug. 10, 2017

(30) Foreign Application Priority Data
Oct. 16, 2014 (SG) .............. 10201406681S

(51) Int. Cl.
*G02B 6/00* (2006.01)
*G02B 6/10* (2006.01)
(Continued)

(52) U.S. Cl.
CPC ........... *G01N 21/3504* (2013.01); *G02B 6/00* (2013.01); *G02B 6/10* (2013.01);
(Continued)

(58) Field of Classification Search
None
See application file for complete search history.

(56) References Cited

U.S. PATENT DOCUMENTS

| 5,444,249 A | 8/1995 | Wong |
| 6,969,857 B2 | 11/2005 | Owen |

(Continued)

FOREIGN PATENT DOCUMENTS

| GB | 2427748 A | 1/2007 |
| JP | 08015540 A * | 1/1996 |

(Continued)

OTHER PUBLICATIONS

International Preliminary Report on Patentability for International Application No. PCT/SG2015/050394 dated Aug. 31, 2016, pp. 1-10.

*Primary Examiner* — Michelle R Connelly
(74) *Attorney, Agent, or Firm* — Winstead, P.C.

(57) ABSTRACT

There is provided an optical waveguide structure, including a substrate, an insulating layer disposed on the substrate whereby the insulating layer includes an air slot formed therein, a first material layer suspended over the air slot whereby the first material layer constitutes a waveguide core of the optical waveguide structure, and a second material layer disposed over the waveguide core whereby the waveguide core is suspended over the air slot by the second material layer. There is also provided an optical gas sensor incorporating the optical waveguide structure and methods of fabrication thereof.

20 Claims, 9 Drawing Sheets

(51) Int. Cl.
*G01N 21/3504* (2014.01)
*G02B 6/12* (2006.01)

(52) U.S. Cl.
CPC .............. *G02B 2006/12097* (2013.01); *G02B 2006/12138* (2013.01); *G02B 2006/12176* (2013.01)

(56) References Cited

U.S. PATENT DOCUMENTS

| | | |
|---|---|---|
| 7,848,599 B2 | 12/2010 | Cunningham et al. |
| 2005/0169566 A1* | 8/2005 | Takahashi ............... G02F 1/011 385/1 |
| 2009/0274418 A1* | 11/2009 | Holzwarth ............. B82Y 20/00 385/30 |
| 2011/0188112 A1 | 8/2011 | Stievater et al. |
| 2012/0223232 A1 | 9/2012 | Kubota |
| 2014/0161387 A1 | 6/2014 | Ide et al. |
| 2014/0264030 A1 | 9/2014 | Lin et al. |
| 2015/0253510 A1* | 9/2015 | Celo .................... G02B 6/3582 385/14 |

FOREIGN PATENT DOCUMENTS

| | | |
|---|---|---|
| JP | H08-15540 A | 1/1996 |
| JP | 2006-030733 A | 2/2006 |
| WO | 2013119981 A1 | 8/2013 |

* cited by examiner

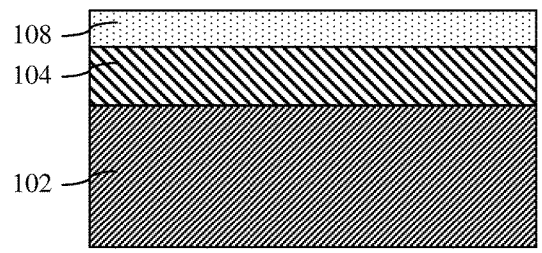
FIG. 5A  SOI wafer
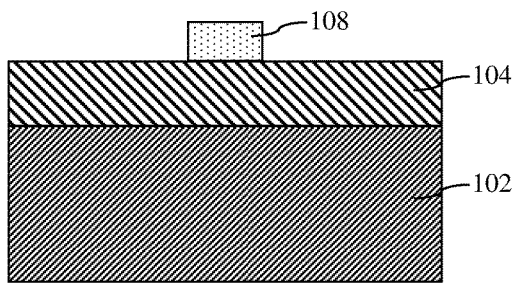
FIG. 5B  Waveguide etching and polish
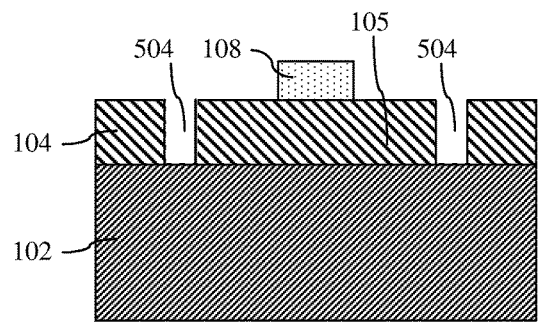
FIG. 5C  Oxide layer etching
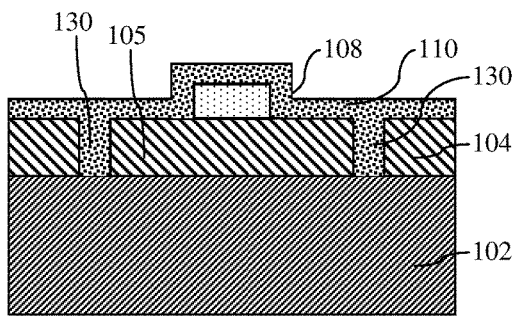
FIG. 5D  Dielectric material deposition
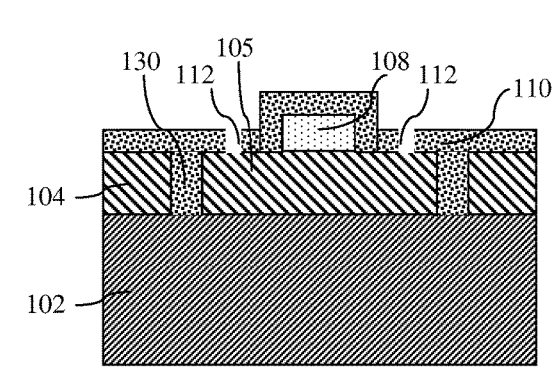
FIG. 5E  Dielectric material layer etching
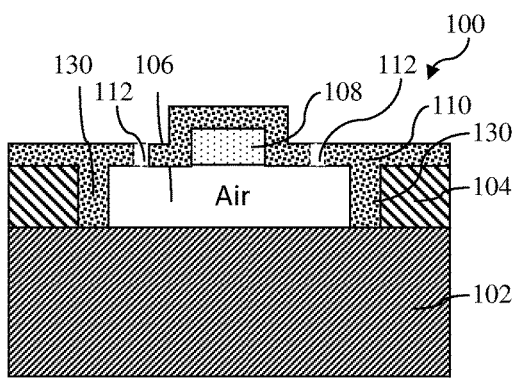
FIG. 5F  Release

OPTICAL WAVEGUIDE STRUCTURE AND OPTICAL GAS SENSOR, AND METHODS OF FABRICATION THEREOF

CROSS-REFERENCE TO RELATED APPLICATION

This application claims the benefit of priority of Singapore Patent Application No. 10201406681S, filed 16 Oct. 2014, the content of which being hereby incorporated by reference in its entirety for all purposes.

TECHNICAL FIELD

The present invention generally relates to an optical waveguide structure and an optical gas sensor, and methods of fabrication thereof.

BACKGROUND

Detection and measurement of gas concentrations using optical absorption of gas molecules is important for both understanding and monitoring a variety of phenomena from industrial processes to environment changes. Although semiconductor and electrochemical gas sensors can be highly sensitive at the low ppm level, they suffer from drift and cross-respond to other gases and changing humidity levels, along with large size and high cost. In contrast, gas sensors based on optical absorption offer, for example, 1) minimal drift as measurements are self-referenced and 2) high gas specificity with zero cross-responses to other gases, as the transduction method makes a direct measurement of a molecule's physical properties (i.e., its absorption at a specific wavelength, or so-called fingerprint wavelength). Therefore, selective detection and multiplexing are some of the attractive features offered by the optical approached.

However, most conventional optical gas sensors are commonly bulky in size and costly, while those compact and inexpensive sensors tend to lack wavelength selectivity or are less sensitive. For example, a conventional optical gas sensor based on either free space optics or fiber optics typically has a relatively large size of around 20 mm in diameter and 18 mm in height, which makes it difficult to realize chip-level integration solution. Furthermore, in conventional optical gas sensors, significant costs are attributed to complex assembling solution and expensive components of light source, detectors and filters.

Gas detection by using photonics waveguide is a promising approach due to its conspicuous advantages, such as ultra-small footprint, flexible integration with conventional electronic integrated circuits, and high operation speed. However, conventional Silicon-on-Insulator (SOI)-based waveguides are not suitable for various gas detections because its waveguide transmission window (transparency) for light propagation is relatively narrow. For example, the longest wavelength that can be supported by a conventional SOI-based waveguide may be about 3.7 μm (based on a waveguide propagation loss less than 2 dBcm$^{-1}$), but the fingerprint absorption wavelengths of a large variety of gas molecules have longer wavelengths. Therefore, it is generally understood in the conventional art that waveguides based on SOI platform is not suitable to be implemented in a gas sensor. On the other hand, waveguides based on Silicon-on-Sapphire (SOS) involve high fabrication costs while not significantly improving the waveguide transmission window for light propagation.

A need therefore exists to provide an optical waveguide structure and an optical gas sensor that seek to overcome, or at least ameliorate, one or more of the deficiencies of conventional optical waveguide structures and optical gas sensors, such as significantly improving the waveguide transmission window (transparency) for light propagation. It is against this background that the present invention has been developed.

SUMMARY

According to a first aspect of the present invention, there is provided an optical waveguide structure, comprising:
 a substrate;
 an insulating layer disposed on the substrate, the insulating layer comprising an air slot formed therein;
 a first material layer suspended over the air slot, the first material layer constituting a waveguide core of the optical waveguide structure; and
 a second material layer disposed over the waveguide core, wherein the waveguide core is suspended over the air slot by the second material layer.

In various embodiments, the second material layer comprises at least one through-hole in fluid communication with the air slot.

In various embodiments, the second material layer is disposed over the waveguide core such that the second material layer covers a top surface and two opposing sidewall surfaces of the waveguide core.

In various embodiments, the second material layer comprises two sidewall portions extending towards the substrate and are spaced apart for forming two opposing sidewalls of the air slot.

In various embodiments, the waveguide core is shaped in the form of a strip.

In various embodiments, the first material layer is a silicon layer.

In various embodiments, the second material layer is a dielectric thin film layer.

In various embodiments, the dielectric thin film layer includes a material selected from a group consisting of aluminum oxide, silicon nitride, germanium, and silicon.

According to a second aspect of the present invention, there is provided a method of fabricating an optical waveguide structure, the method comprising:
 providing a structure comprising a substrate, an insulating layer disposed on the substrate, and a first material layer disposed on the insulating layer;
 etching the first material layer to form a waveguide core of the optical waveguide structure;
 disposing a second material layer over the waveguide core; and
 removing a portion of the insulating layer under the waveguide core to form an air slot therein and to release the waveguide core such that the waveguide core is suspended over the air slot by the second material layer.

In various embodiments, the method further comprises forming at least one through-hole in the second material layer to be in fluid communication with the portion of the insulating layer to be removed.

In various embodiments, disposing a second material layer over the waveguide core comprises disposing the second material layer to cover a top surface and two opposing sidewall surfaces of the waveguide core.

In various embodiments, the method further comprises etching the insulating layer to form two trenches therein which are spaced apart, wherein disposing a second material layer over the waveguide core further comprises disposing the second material layer into the two trenches to form two sidewall portions which are spaced apart and constitute two opposing sidewalls of the air slot formed in said removing a portion of the insulating layer.

In various embodiments, the waveguide core is shaped in the form of a strip.

In various embodiments, the first material layer is a silicon layer.

In various embodiments, the second material layer is a dielectric thin film layer.

In various embodiments, the dielectric thin film layer includes a material selected from a group consisting of aluminum oxide, silicon nitride, germanium, and silicon.

According to a third aspect of the present invention, there is provided an optical gas sensor comprising:
  a light source configured to emit light;
  a gas sensing section comprising an optical waveguide structure according to the first aspect of the present invention, the optical waveguide structure being arranged to receive the light from the light source and transmit the light received through the optical waveguide structure; and
  a light detector arranged to receive the light transmitted from the optical waveguide structure and configured to detect a gas in the gas sensing section based on the light received.

In various embodiments, the optical gas sensor further comprises a tunable filter configured to receive the light from the light source and selectively transmit the light having a predetermined wavelength to the optical waveguide structure.

In various embodiments, the optical gas sensor further comprises a cap wafer for enclosing a side of the optical gas sensor on which the gas sensing section is disposed to form a chamber therein, the cap wafer comprising one or more apertures in fluid communication with the chamber.

According to a fourth aspect of the present invention, there is provided a method of fabricating an optical gas sensor, the method comprising:
  disposing a light source on a substrate, the light source configured to emit light;
  forming a gas sensing section on the substrate, the gas sensing section comprising an optical waveguide structure according to the first aspect of the present invention, the optical waveguide structure being arranged to receive the light from the light source and transmit the light received through the optical waveguide structure; and
  disposing a light detector on the substrate, the light detector arranged to receive the light transmitted from the optical waveguide structure and configured to detect a gas in the gas sensing section based on the light received.

BRIEF DESCRIPTION OF THE DRAWINGS

Embodiments of the present invention will be better understood and readily apparent to one of ordinary skill in the art from the following written description, by way of example only, and in conjunction with the drawings, in which:
FIGS. 5A to 5F depict an exemplary method of fabricating the optical waveguide structure shown in FIG. 1 according to an example embodiment of the present invention.

DETAILED DESCRIPTION

Embodiments of the present invention provide an optical waveguide structure and an optical gas sensor that seek to overcome, or at least ameliorate, one or more of the deficiencies of conventional optical waveguide structures and optical gas sensors.

As described in the background, there are various limitations associated with conventional waveguides used for sensing/detecting gas. For example, in conventional Silicon-on-Insulator (SOI)-based waveguides, a major limitation is their narrow waveguide transmission window for light propagation. As a result, such conventional SOI-based waveguides are not suitable to be implemented in a gas sensor since the fingerprint absorption wavelengths of a large variety of gas molecules are longer than the wavelengths which can be supported by such conventional SOI-based waveguides. Embodiments of the present invention advantageously provide an optical waveguide structure based on an SOI platform having a significantly wider waveguide transmission window. This technical effect advantageously makes the optical waveguide structure suitable to be implemented in an optical gas sensor for detecting a wide range of gas types/species. This and other advantages associated with the optical waveguide structure according to embodiments of the present invention will become more apparent from the description herein.

Figure 1:
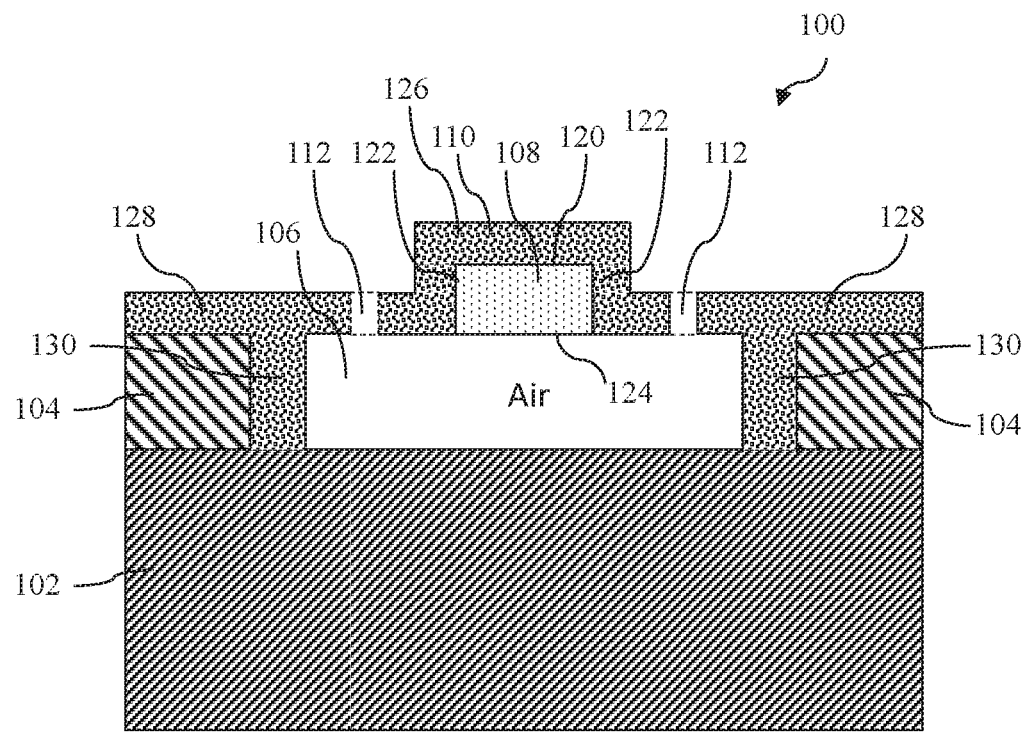
FIG. 1 depicts a schematic drawing of an optical waveguide structure according to an embodiment of the present invention.

FIG. 1 depicts a schematic drawing of an optical waveguide structure 100 according to an embodiment of the present invention. In the embodiment, as shown, the optical waveguide structure 100 comprises a substrate 102, an insulating layer 104 disposed on the substrate 102 whereby the insulating layer 104 comprises an air slot 106 formed therein, a first material layer 108 suspended over the air slot 106 whereby the first material layer 108 constitutes a waveguide core of the optical waveguide structure 100, and a second material layer 110 disposed over the waveguide core 108 whereby the waveguide core 108 is suspended over the air slot 106 by the second material layer 110. It will be appreciated by a person skilled in the art that the air slot 106 may be referred to by other names, such as air cavity, air channel, or the like. In various example embodiments, the substrate 102 is a silicon substrate, the insulating layer 104 is a silicon dioxide ($SiO_2$) layer, and the first material layer 108 is a silicon layer. Therefore, in such various embodiments, the optical waveguide structure 100 is based on an SOI platform. In various example embodiments, the second material layer 110 is a dielectric thin film layer made of, for example and without limitation, aluminum oxide (e.g., $Al_2O_3$), silicon nitride (e.g., $Si_3N_4$), germanium, or silicon (e.g., crystal or amorphous Si).

With the above structural configuration, the optical waveguide structure 100 advantageously possesses a significantly wider waveguide transmission window (i.e., significantly wider wavelength transparency) for light propagation. For example, in the case where the second material layer 110 supporting/holding the core waveguide 108 is made of $Si_3N_4$, the waveguide transmission window of the optical waveguide structure 100 has been found to significantly improve to a range of about 1.2 µm to 6.6 µm (based on a waveguide propagation loss within 2 $dBcm^{-1}$). In contrast, as mentioned in the background, the longest wavelength that can be supported by a conventional SOI-based waveguide may be about 3.7 µm (based on a waveguide propagation loss within 2 $dBcm^{-1}$), and in particular, from about 1.2 µm to about 3.7 µm. Therefore, with the above structural configuration, the optical waveguide structure 100 is capable of/suitable for use in an optical gas sensor for detecting a significantly wider range of gas types/species. For example and without limitation, with the improved waveguide transmission window for light propagation, the optical waveguide structure 100 is suitable for use in an optical gas sensor for detecting $CO_2$ (strong absorption peak at 4.26 µm), CO (strong absorption peak at 4.65 µm), $SO_2$ (strong absorption peak at 4 µm), and $CH_3$ (strong absorption peak at 6.1 µm), whereas the above-mentioned conventional SOI-based waveguide would not suitable since the above types of gas molecules all have fingerprint absorption wavelengths which are outside of its waveguide transmission window.

Figure 2:
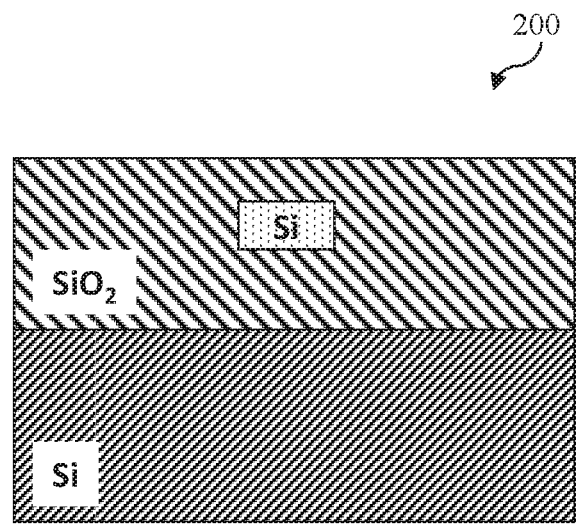
FIG. 2 depicts a schematic drawing of a conventional SOI-based buried strip waveguide.

Without wishing to be bound by theory, but the optical waveguide structure 100 is advantageously configured such that the waveguide core 108 is not interfaced with a material layer that would cause the waveguide core 108 to have an undesirably limited waveguide transmission window, such as the $SiO_2$ layer 104. For example, in the case of the waveguide core being interfaced with a $SiO_2$ layer as with conventional SOI-based waveguides, the waveguide transmission window is limited by the $SiO_2$ layer to only be able to support a wavelength of up to 3.7 µm due to the large absorption loss of the $SiO_2$ layer for wavelengths above 3.7 µm. As an example and for illustration purposes only, FIG. 2 depicts a schematic drawing of a conventional SOI-based buried strip waveguide 200 whereby the strip waveguide core is buried in the $SiO_2$ layer. In such a conventional waveguide 200, the waveguide transmission window is undesirably limited by the $SiO_2$ layer surrounding the waveguide core to only be able support a wavelength of up to 3.7 µm.

In contrast, embodiments of the present invention do not dispose the waveguide core in or directly on, for example, the $SiO_2$ layer, but configure the waveguide core 108 to be suspended over an air slot 106 as illustrated in FIG. 1. With such a configuration, the waveguide core 108 is advantageously isolated from the $SiO_2$ layer. In particular, the waveguide core 108 is suspended over the air slot 106 by a material layer 110 disposed over the waveguide core 108 and the insulating layer 104 as shown in FIG. 1. As the material layer 110 is interfaced with the waveguide core 108, the material of the material layer 110 is selected so as to provide the waveguide core 108 with a sufficiently wide waveguide transmission window. For example and without limitation, if the second material layer 110 is made of a dielectric material $Si_3N_4$ and the waveguide core 108 is made of Si (i.e., $Si_3N_4/Si$), the waveguide transmission window has been found to significantly improve to a range of about 1.2 µm to about 6.6 µm (based on a waveguide propagation loss within 2 $dBcm^{-1}$). As mentioned hereinbefore, other suitable dielectric materials for the second material layer 110 may be selected, including but not limited to aluminum oxide (e.g., $Al_2O_3$), germanium, and silicon (e.g., crystal or amorphous Si).

In various embodiments, as illustrated in FIG. 1, the second material layer 110 comprises at least one through-hole (release hole) 112 in fluid communication with the air slot 106. The through-hole 112 is formed in the second material layer 100 to enable the removal of the portion of the insulating layer 104 under the waveguide core 108 for forming the air slot 106 therein and to release the waveguide core 108 such that the waveguide core 108 is suspended over the air slot 106 by the second material layer 110. In particular, the through-hole 112 provides a passage for an etchant to reach and remove the above-mentioned portion of the insulating layer 104 by etching. After the air slot 106 under the waveguide core 108 is formed, the through-hole 112 may also serve as a passage for gas to flow in and out of the air slot 106, which enhances gas diffusion in gas sensing.

As shown in FIG. 1, the second material layer 110 is disposed over the waveguide core 108 such that the second material layer 110 covers a top surface 120 and two opposing sidewall surfaces 122 of the waveguide core 108. Therefore, the waveguide core 108 is surrounded by the second material layer 110 except at the bottom surface 124 thereof which is exposed to the air/gas in the air slot 106. In the embodiment of FIG. 1, it can be seen that the second material layer 110 is disposed directly over (directly on) the waveguide core 108 and the insulating layer 104. The portion of the second material layer 110 covering (disposed on) the waveguide core 108 may be referred to as a waveguide core covering portion 126, and the portion of the second material layer 110 covering (disposed on) the insulating layer 110 may be referred to as a planar portion 128. In addition, as shown in FIG. 1, the second material layer 110 further comprises two sidewall portions 130 extending from the planar portion 128 toward the substrate 102. The two sidewall portions 130 are spaced apart for forming two opposing sidewalls of the air slot 106 to be created when the portion of the insulating layer 104 therebetween and under the waveguide core 108 is subsequently removed. Accordingly, it can be understood that the two sidewall portions 130 may be arranged/configured to be spaced apart by a distance as desired for setting a width of the air slot 106 to be formed. After the portion of the insulating layer 104 under the waveguide core 108 and bounded by the second material layer 110 is removed, the air slot 106 would be formed and the waveguide core 108 would be released and suspended by the second material layer 110 over the air slot 106. Therefore, the second material layer 110 provides a support/frame structure for holding/suspending the waveguide core 108 above the air slot 106.

Figure 3:
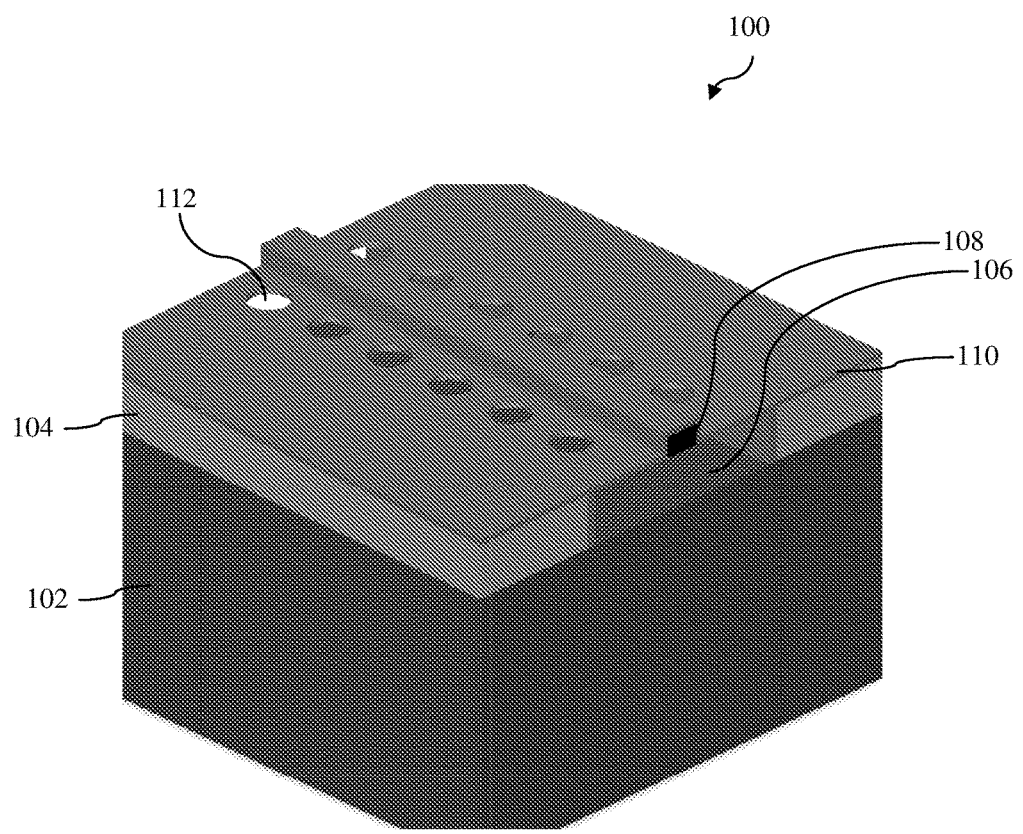
FIG. 3 depicts a perspective view of the optical waveguide structure shown in FIG. 1.

For illustration purposes only, FIG. 3 depicts a perspective view of the optical waveguide structure 100 shown in FIG. 1. In various embodiments, the second material layer 110 of the optical waveguide structure 100 comprises two rows/arrays of through-holes (release holes) 112 formed/arranged therein such that the waveguide core 108 is located between the two rows/arrays of through-holes 112 as shown in FIG. 3. In various embodiments, the waveguide core 108 is shaped in the form of a strip, and in such embodiments, the optical waveguide structure 100 may thus be referred to as an optical strip waveguide structure.

Accordingly, the optical waveguide structure 100 may be referred to as a free-standing optical waveguide structure and can be configured to be suitable for gas sensing in, for example, the Mid-IR wavelength region. Compared to a conventional strip waveguide structure buried in silicon dioxide ($SiO_2$) (e.g., see FIG. 2), the free-standing optical waveguide structure 100 provides lower optical loss and wider wavelength transmission window. Therefore, the free-standing optical waveguide structure 100, for example, successfully overcomes the limitation from the $SiO_2$ material associated with conventional SOI-based waveguides. As will be described later, an optical gas sensor incorporating the free-standing optical waveguide structure 100 may also be implemented according various embodiments of the present invention, offering the sensor with ultra-compact size, cost effectiveness, and wafer-level packaging capability. It can be understood that the optical gas sensor has a wide variety of applications including, for example and without limitation, indoor air quality supervision, disease diagnosis and treatment, personal medical care, and industrial safety.

Figure 4:
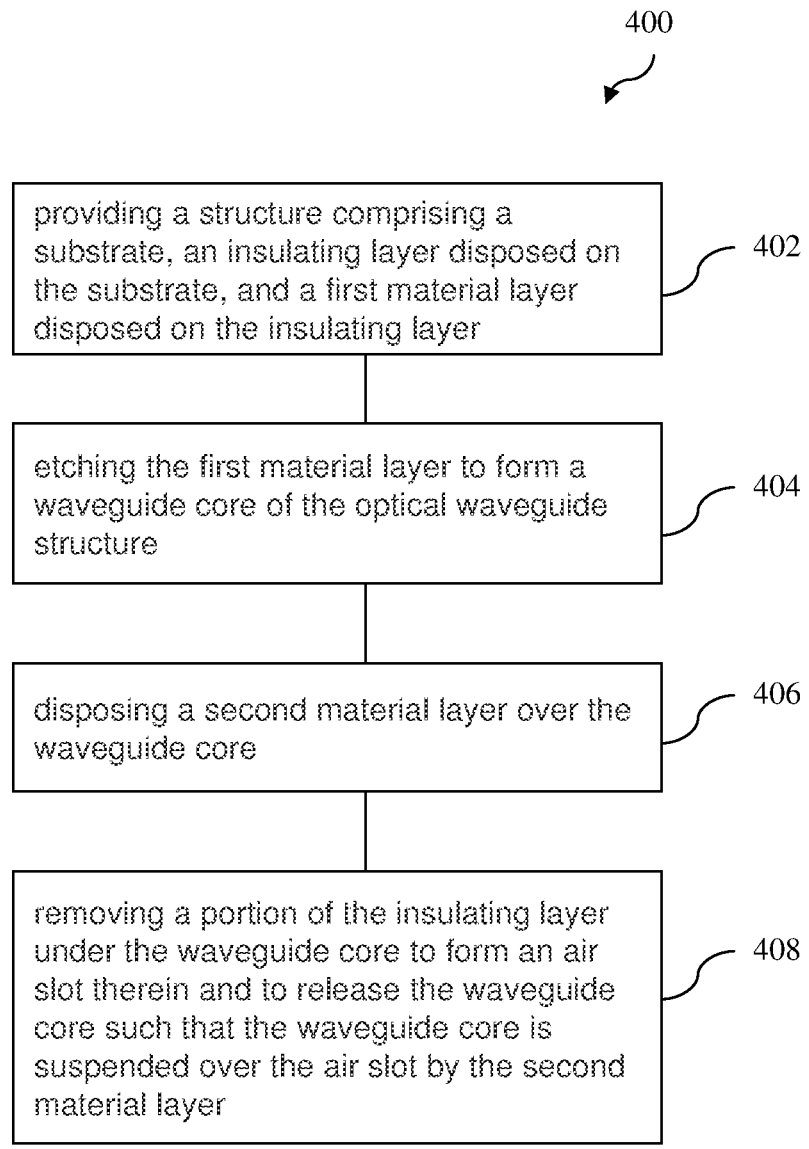
FIG. 4 depicts a general flow diagram of a method of fabricating the optical waveguide structure according to an embodiment of the present invention.

FIG. 4 depicts a general flow diagram of a method 400 of fabricating the optical waveguide structure according to an embodiment of the present invention. The method 400 comprises a step 402 of providing a structure comprising a substrate 102, an insulating layer 104 disposed on the substrate 102, and a first material layer 108 disposed on the insulating layer 104, a step 404 of etching the first material layer 108 to form a waveguide core of the optical waveguide structure 100, a step 406 of disposing a second material layer 110 over the waveguide core 108, and a step 408 of removing a portion 105 of the insulating layer 104 under the waveguide core 108 to form an air slot 106 therein and to release the waveguide core 108 such that the waveguide core 108 is suspended over the air slot 106 by the second material layer 110.

In order that the present invention may be readily understood and put into practical effect, an exemplary method of fabricating the optical waveguide structure 100 will now be described with reference to FIGS. 5A to 5F according to an example embodiment of the present invention. In the example embodiment, the optical waveguide structure 100 is formed on an SOI platform using a CMOS compatible fabrication technology.

As shown in FIG. 5A, the fabrication method may start with a SOI wafer comprising a silicon layer (first material layer) 108 and a buried oxide layer (insulating layer) 104 on a silicon substrate 102.

Subsequently, as shown in FIG. 5B, the silicon layer 108 is etched to pattern the waveguide core. In the example embodiment, the silicon layer 108 is etched to shape the waveguide core in the form of a strip. Various etching techniques known in the art may be applied to shape the waveguide core such as but not limited to chemical dry etching, using, for example, tetrafluoromethane, sulfur hexafluoride, or chlorine gas, to define the shape of the waveguide to be formed. After etching, the exposed surfaces of the waveguide core 108 and the oxide layer 104 may also be polished in a manner known to a person skilled in the art.

Next, as shown in FIG. 5C, the oxide layer 104 is etched to form two trenches 504 therein and are spaced apart from each other. In this regard, the two trenches 504 are spaced apart for defining two opposing sidewalls of the air slot 106 to be formed in a subsequent step (see FIG. 5F). That is, the two trenches 504 are arranged to be spaced apart by a distance as desired for setting a width of the air slot 106 to be formed.

Next, as shown in FIG. 5D, a dielectric material such as aluminum oxide (e.g., $Al_2O_3$) is deposited directly over the waveguide core 108 and the oxide layer 104 for forming dielectric thin film layer 110 thereon. Various deposition techniques known in the art may be applied to deposit the dielectric material such as but not limited to chemical vapor deposition (CVD) and atomic layer deposition (ALD). In this deposition, the dielectric material would also fill the two trenches 504 created in a previous step (see FIG. 5C) so as to form two sidewall portions 130 which are spaced apart. These two sidewall portions 130 would constitute two opposing sidewalls of the air slot 106 to be formed. As mentioned hereinbefore, other suitable dielectric materials for the material layer 110 may also be selected, including but not limited to silicon nitride (e.g., $Si_3N_4$), germanium, or silicon (e.g., crystal or amorphous Si).

Next, as shown in FIG. 5E, the material layer 110 is etched to form a plurality of through-holes 112 in fluid communication with the portion 105 of the oxide layer 104 to be removed so as to create a release window in the material layer 110. In the example embodiment, the release window is in the form of two rows/arrays of through-holes 112 in the material layer 110 with the waveguide core 108 located between the two rows/arrays of through holes 112 as for example illustrated in FIG. 3. Thereafter, as shown in FIG. 5F, the portion 105 of the buried oxide layer 104 under the waveguide core 108 and bounded by the material layer 110 is removed to obtain the free-standing optical waveguide 100 by using a release etch process. Release etch process is known in the art (e.g., using vapor hydrogen fluoride (HF) as an etchant) and thus need not be described in detail herein.

Figure 6A:
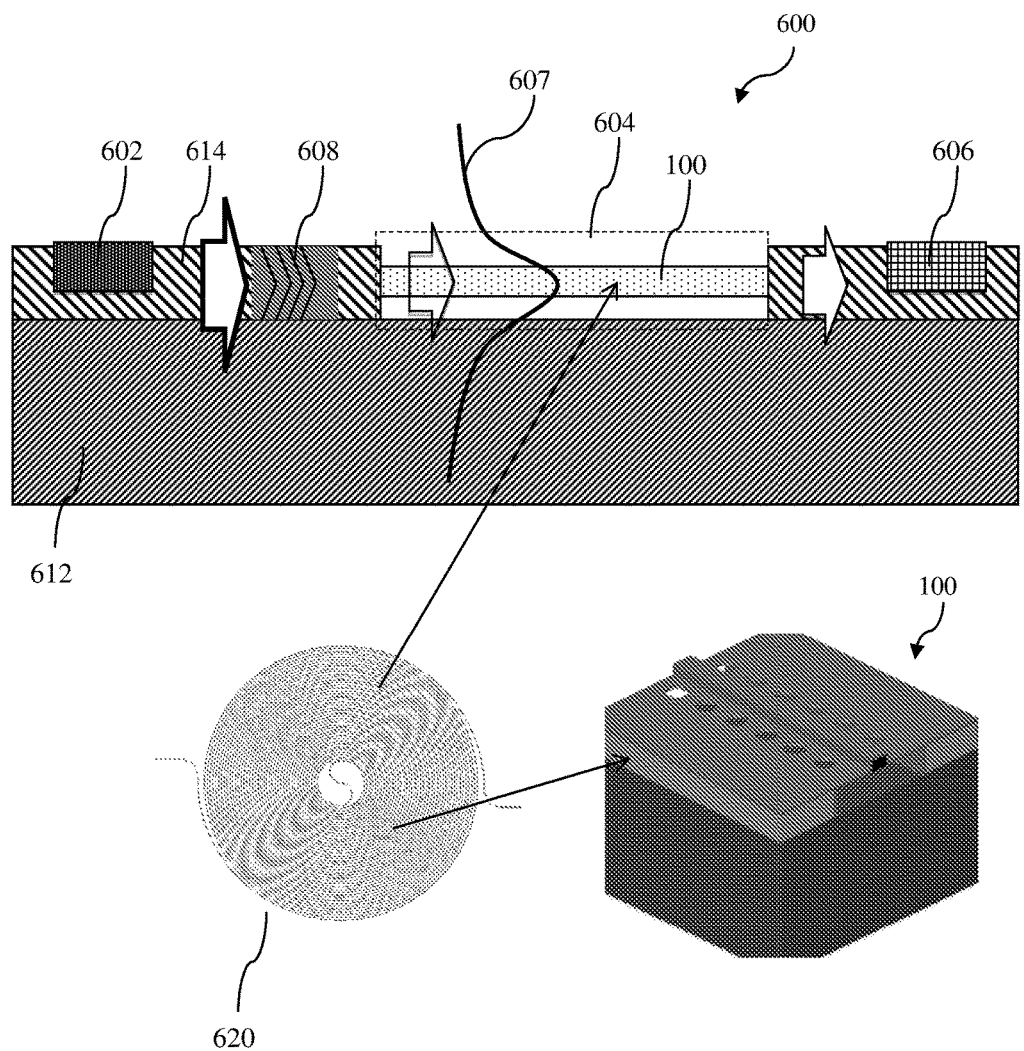
FIG. 6A depicts a schematic drawing of an optical gas sensor according to an example embodiment of the present invention, incorporating the optical waveguide structure shown in FIG. 1.

As mentioned hereinbefore, the optical waveguide structure 100 according to embodiments of the present invention may be implemented in an optical gas sensor for detecting/sensing gas, and in particular, identifying gas type(s) and/or determining gas concentration. FIG. 6A depicts a schematic drawing of an optical gas sensor 600 according to an example embodiment of the present invention, incorporating the optical waveguide structure 100. In the example embodiment, the optical gas sensor 600 comprises a light source 602 configured to emit light, a gas sensing section/region 604 comprising the optical waveguide structure 100 whereby the optical waveguide structure 100 is arranged to receive the light from the light source 602 and transmit the light received through the optical waveguide structure 100, and a light detector 606 arranged to receive the light transmitted from the optical waveguide structure 100 and configured to detect a gas in the gas sensing section 604 based on the light received, such as the presence of a type of gas and/or a concentration of the gas. The principle for the detection of a type of gas and the measurement of a gas concentration using the characteristic optical absorption of the gas specie/molecules are well known in the art and thus need not be described in detail herein. For example, generally, when light is transmitted along the optical waveguide structure 100, an evanescent field 607 is generated and portions thereof outside the optical waveguide structure 100 interact with and measure the optical absorption of any gas specie/molecules (that is, based on the absorbing wavelength(s) characteristic of the gas specie/molecules, which may be referred to as its fingerprint absorption spectra) present around the optical waveguide structure 100 (e.g., in the gas sensing section 604). Therefore, an optical signal (light) having a wavelength selected based on the absorption fingerprint/characteristic of the gas specie/molecules desired to be detected (i.e., wavelength which overlaps with the strong absorption peak of the gas specie/molecules) can interact with the gas specie/molecules and the power/intensity of the optical signal would thus be attenuated. The concentration and/or the presence of the gas specie/molecules can then be determined from the light power/intensity attenuation based on, for example, the Beer-Lambert law known in the art. For example, the change in intensity of the light received by the light detector 606 due to light absorption by the gas specie/molecules is proportional to the gas concentration and thus reveals quantitative information regarding the concentration of the gas specie/concentration in the gas sensing region 604.

In various embodiments, the optical gas sensor 600 preferably further comprises a tunable filter 608 configured to receive the light from the light source 602 and selectively transmit the light having a predetermined wavelength to the optical waveguide structure 100. The tunable filter 608 may be configured to have a wavelength tuning range based on the variety of gas molecules desired to be detected, such as but not limited to about 2 µm to about 7 µm, or about 2 µm to about 5 µm. For example, the tunable filter 608 may be configured to transmit light having a wavelength selected based on (overlaps with) the fingerprint wavelength (strong absorption peak) of the gas specie/molecules desired to be detected. In various embodiments, the light source 602 and the light detector 606 may be fabricated on the silicon chip/substrate 612 or hybrid integrated (i.e., bonded) on the silicon chip/substrate 612.

Figure 6B:
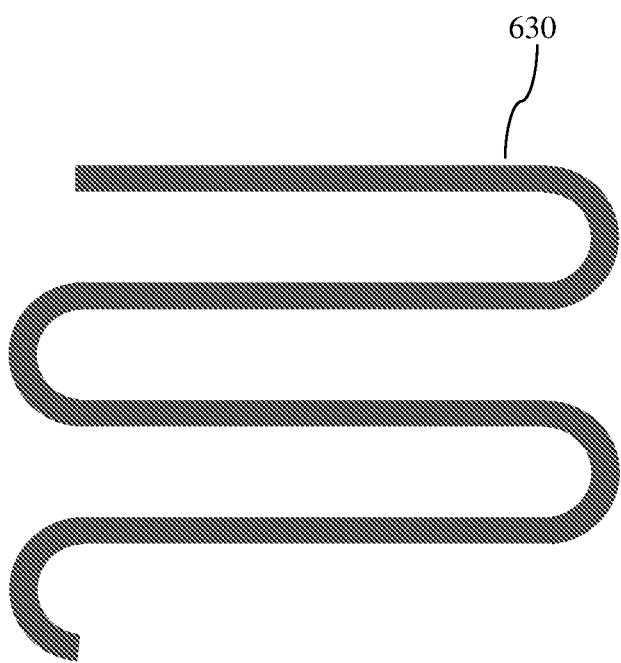
FIG. 6B depicts another type of waveguide pattern according to an example embodiment of the present invention.

According to an example embodiment, the optical waveguide structure 100 is arranged/configured to form a spiral pattern 620 as illustrated in FIG. 6A. The spiral pattern 620 enables a much longer optical path through the optical waveguide structure 100 to be created within a relatively small area/space, thereby allowing an ultra-compact sensor to be fabricated. For example and without limitation, based on the spiral pattern 620, a 1 m length optical path may be obtained within a 1 mm² area on a chip. Although the spiral pattern 620 may be preferred according to embodiments of the present invention, it will be understood that the present invention is not limited to the spiral pattern and the optical waveguide structure 100 may be arranged/configured to form other patterns as long as the pattern enables a long optical path to be formed on a relatively small area/space. As an example and without limitation, the optical waveguide structure 100 may be arranged/configured to form a folded pattern 630 as schematically illustrated in FIG. 6B. It can also be appreciated from FIG. 6A that the functional elements/components of the optical gas sensor 600 (i.e., the tunable filter 608, the optical waveguide structure 100, and the light detector 606) are disposed/formed on the same substrate 612, which advantageously results in an integrated optical gas sensor 600 having a compact chip size.

As an example, with the configuration of the optical gas sensor 600 as shown in FIG. 6A, the light from the light source 602 is firstly coupled into a silicon waveguide 614. Then, the tunable filter 608 (such as ring filter, disk filter, Fabry-Pérot filter, and so on) is used to select a certain wavelength which overlays with the fingerprint wavelength of gas specie. By way of examples only and without limitation, the tunable filter 608 may select a wavelength of 4.24 µm for detecting $CO_2$ gas or a wavelength of 4.64 µm for detecting CO gas so that the light received by the optical waveguide structure 100 can fully interact with gas molecules of interest to be detected (with specific fingerprint wavelength absorbed) and would then carry on the signal/information (e.g., light power/intensity attenuation) to the light detector 606 for, e.g., detecting the gas concentration. Thereafter, the light signal reaches the light detector 606 which is configured to generate an electrical signal indicative of the presence and/or the concentration of the gas based on the change in intensity/power in the fingerprint wavelength regions of the light received. Accordingly, the optical waveguide-based detection can be used to replace conventional free space configurations for high sensitivity detection and low power consumption.

Accordingly, from FIG. 6A, it can be appreciated the optical gas sensor 600 is advantageously configured such that the sensing light signal and reference light signal can share a common waveguide 100 and can be switched by the tunable filter 608. For example, the light source 602 may emit light in the Mid-IR wavelength region and the light is passed through the tunable filter 608. Two wavelengths (a first wavelength being the fingerprint wavelength of the target gas and a second wavelength being a reference wavelength) are selected periodically and transmitted along the optical waveguide structure 100. The light transmitted through the optical waveguide structure 100 and received by the light detector 606 is then processed to detect the gas concentration. Various signal processing techniques known in the art for determining the gas concentration based on the received sensing light signal and reference light signal may be applied. For example and without limitation, a basic signal processing technique for determining the gas concentration is based on dividing the received sensing light signal by the reference light signal. In various embodiments, multi-gas detection can also be realized by using the tunable filter 608 to select different optical wavelength based on the fingerprint wavelength of the target gases desired to be detected.

In various embodiments, the tunable filter 608 may be tuned by thermal, electrical or mechanical mechanisms. These mechanisms are known in the art and thus need not be described herein.

Figure 7:
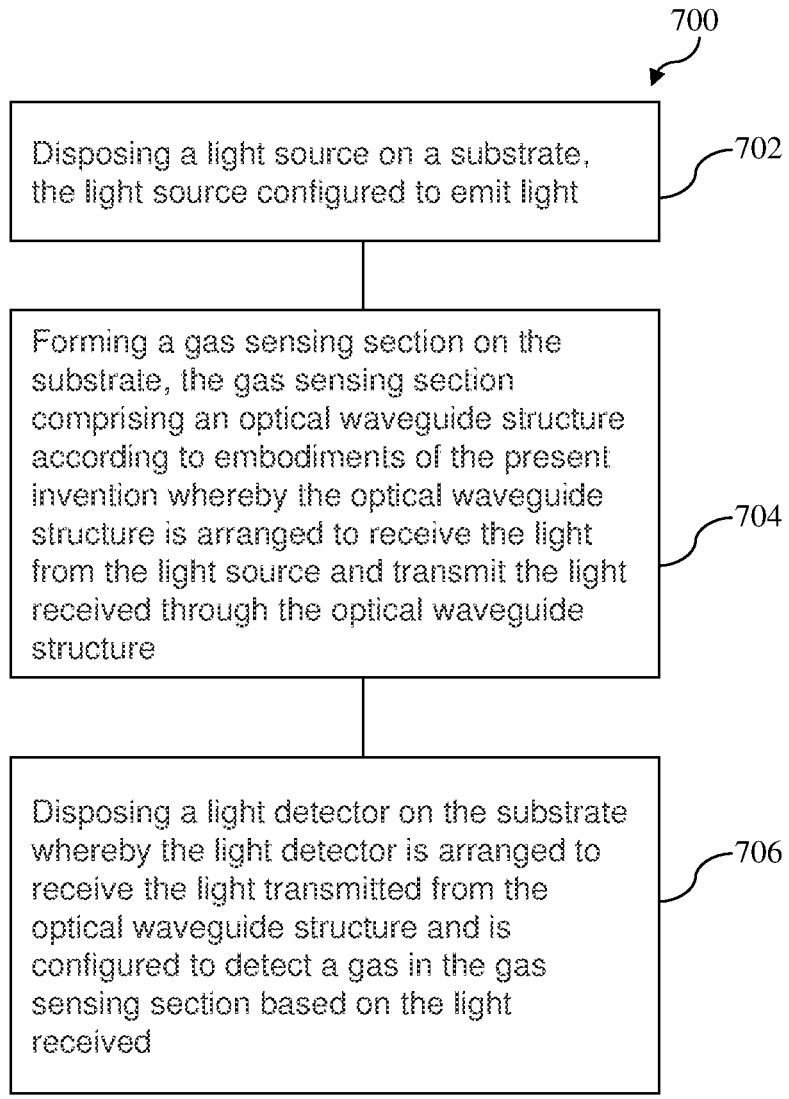
FIG. 7 depicts a general flow diagram of a method of fabricating the optical gas sensor according to an embodiment of the present invention.

FIG. 7 depicts a general flow diagram of a method 700 of fabricating the optical gas sensor 600 according to an embodiment of the present invention. The method 700 comprises a step 702 of disposing a light source 602 on a substrate 612 (e.g., silicon substrate), the light source 612 being configured to emit light, a step 704 of forming a gas sensing section 604 on the substrate 612, the gas sensing section 604 comprising the optical waveguide structure 100 whereby the optical waveguide structure 100 is arranged to receive the light from the light source 602 and transmit the light received through the optical waveguide structure 100, and a step 706 of disposing a light detector 606 on the substrate 612 whereby the light detector 606 is arranged to receive the light transmitted from the optical waveguide structure 100 and is configured to generate an electrical signal based on the light received for detecting a gas in the gas sensing section 604.

Figure 8:
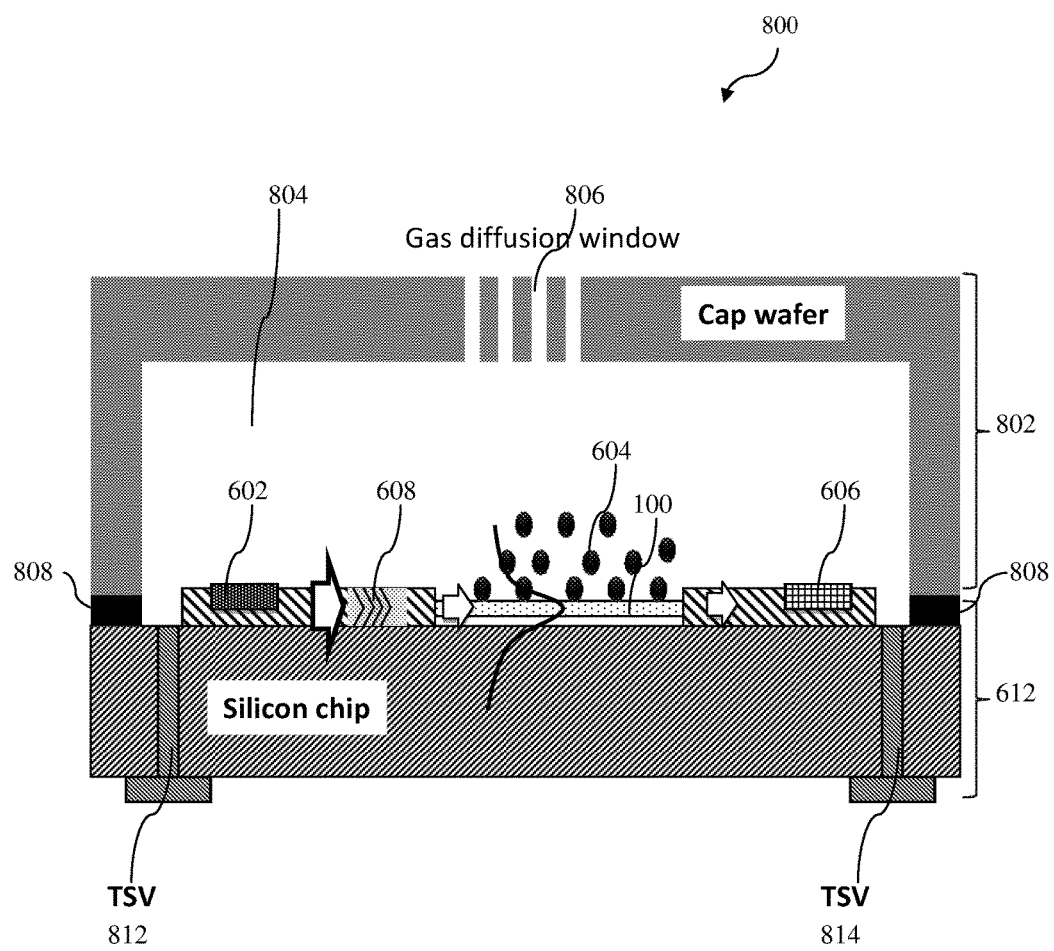
FIG. 8 depicts a schematic drawing of a wafer-level packaged optical gas sensor according to an example embodiment of the present invention.

According to an embodiment of the present invention, the optical gas sensor is packaged via a wafer-level chip scale package (WLCSP) technique to provide a wafer-level package enabled integrated optical gas sensor for compact and low cost solution. This can be achieved because the fabrication of the optical gas sensor 600 is compatible with the CMOS process and the chip size obtained is, for example, only several $mm^2$. FIG. 8 depicts a schematic drawing of a wafer-level packaged optical gas sensor 800 according to the embodiment. In the embodiment, the optical gas sensor 600 further comprises a cap wafer 802 for enclosing/covering a side of the optical gas sensor 600 on which the gas sensing section 604 is formed to form a chamber 804 therein, and in particular, to form a gas-photo interaction chamber. The cap wafer 804 comprises one or more apertures 806 in fluid communication with the chamber 804 (i.e., gas inlets/outlets) for gas diffusion in gas sensing. For example, the cap wafer 802 may be affixed to the optical gas sensor 600 via solder 808 as illustrated in FIG. 8. In addition, the substrate 612 comprises two vias (through-silicon vias (TSVs)) therein, in particular, a first via 812 having a metal conductor therein communicatively coupled to the light source 602 and a second via 814 having a metal conductor therein communicatively coupled to the light detector 606. That is, the TSVs 812, 814 function as electrical interconnects through the semiconductor substrate 612.

Accordingly, embodiments of the present invention advantageously provides an optical waveguide structure 100 having a significantly wider wavelength transmission window while enabling the fabrication of an on-chip integrated optical gas sensor having an ultra-compact size and wafer-level packaging capability in a cost effective manner. For example, the optical waveguide structure 100 can be configured to have low loss in the Mid-IR wavelength region and strong evanescent optical power. In various embodiments, a chip-scale multi-gas sensor can be obtained with high fidelity (self calibrated using wavelength switch) and multi-gas sensing capability (wide wavelength tuning range). In various embodiments, a coating-free gas sensor can be obtained resulting in longer life time and low drift (no carry-over effect) and low cross-contamination (selectivity provided by gas absorption spectrum, not coating chemistry).

Figure 9A:
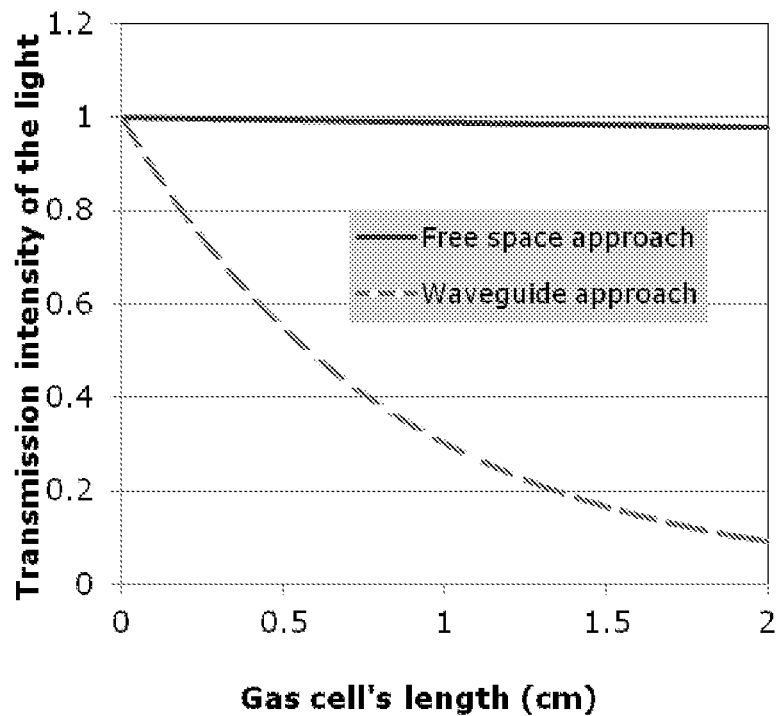
FIG. 9A depicts a plot comparing the effective light absorption for the conventional free space approach and the waveguide approach according to an example embodiment of the present invention.
Figure 9B:
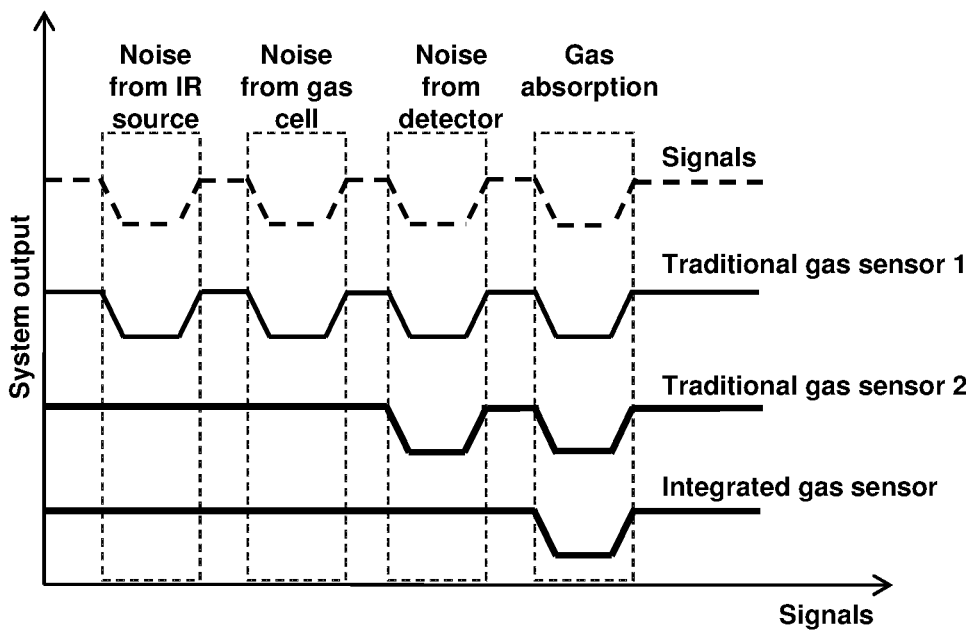
FIG. 9B depicts a plot comparing various parameters of conventional gas sensors and the integrated optical gas sensor according to an example embodiment of the present invention.

FIG. 9A depicts a plot comparing the effective light absorption for the conventional free space approach and the waveguide approach according to an example embodiment of the present invention. FIG. 9A shows that compared to the free space approach, light absorption can be obtained in a shorter gas cell's length (sensing channel's length) for the waveguide approach. This shows that a very short gas cell with high sensitivity detection can be obtained based on the waveguide approach according to the example embodiment of the present invention. FIG. 9B depicts a plot comparing various parameters of conventional gas sensors and the integrated optical gas sensor according to an example embodiment of the present invention. Traditional gas sensor 1 has one sensing light channel (gas cell), one light source, and one light detector, but no reference channel. In traditional gas sensor 1, all of the noises from the light source, sensing channel, and the light detector can affect its performance. Therefore, traditional gas sensor 1 may be regarded being based on a no noise reduction approach. Traditional gas sensor 2 has both sensing light channel and reference light channel, one light source and two light detectors. In traditional gas sensor 2, a gas sensing signal and a reference signal can be readout simultaneously from the two light detectors. This can reduce the noise from the sensing channel and the light source, but the noise from the light detectors still exist as the performances of the two light detectors cannot be the same. FIG. 9A shows that compared to traditional gas sensors 1 and 2, noises from light source, sensing channel (gas cell) and light detector of the integrated optical gas sensor according to the example embodiment can be greatly reduced since both sensing wavelength and reference wavelength are sharing the same light source, the same gas sensing channel, and the same light detector.

It can be understood that the optical gas sensor described according to embodiments of the present invention has a wide variety of applications including, for example and without limitation, medical applications (e.g., detecting $CO_2$ with fast speed and high sensitivity for respiration rate/depth detection applications), automotive industry (e.g., detection of polluting gases from vehicles), indoor air quality monitoring (e.g., for smart home and automotive cars), manufacturing process control (e.g., in agriculture and food industry), gas leakage detection in chemical process industry and energy industry for safety conscious, and consumer electronics (e.g., smart phones and wearable consumer electronics).

Throughout the present specification, it can be understood that when a layer or element is referred to as being "on" another layer or element, the layer or element can be directly on another layer or element (i.e., without any intermediate/intervening layers or elements therebetween) or indirectly on another layer or element (i.e., with one or more intermediate layers or elements therebetween). Therefore, unless stated otherwise, such an expression should be interpreted to cover both cases. It should also be understood that any terms such as "top", "bottom", "base", "down", "sideways", "downwards", or the like, when used in the present specification are used for convenience and to aid understanding of relative positions or directions, and not intended to limit the orientation of the optical waveguide structure or optical gas sensor.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:
1. An optical waveguide structure, comprising:
a substrate;
an insulating layer disposed on the substrate, the insulating layer comprising an air slot formed therein;
a first material layer suspended over the air slot of the insulating layer, the first material layer constituting a waveguide core of the optical waveguide structure; and
a second material layer disposed over the waveguide core, wherein the waveguide core is suspended over the air slot of the insulating layer by the second material layer, and a surface of the waveguide core is exposed to the air slot of the insulating layer.

2. The optical waveguide structure according to claim 1, wherein the second material layer comprises at least one through-hole in fluid communication with the air slot.

3. The optical waveguide structure according to claim 1, wherein the second material layer is disposed over the waveguide core such that the second material layer covers a top surface and two opposing sidewall surfaces of the waveguide core.

4. The optical waveguide structure according to claim 1, wherein the second material layer comprises two sidewall portions extending towards the substrate and are spaced apart for forming two opposing sidewalls of the air slot.

5. The optical waveguide structure according to claim 1, wherein the waveguide core is shaped in the form of a strip.

6. The optical waveguide structure according to claim 1, wherein the first material layer is a silicon layer.

7. The optical waveguide structure according to claim 1, wherein the second material layer is a dielectric thin film layer.

8. The optical waveguide structure according to claim 7, wherein the dielectric thin film layer includes a material selected from a group consisting of aluminum oxide, silicon nitride, germanium, and silicon.

9. A method of fabricating an optical waveguide structure, the method comprising:
   providing a structure comprising a substrate, an insulating layer disposed on the substrate, and a first material layer disposed on the insulating layer;
   etching the first material layer to form a waveguide core of the optical waveguide structure;
   disposing a second material layer over the waveguide core; and
   removing a portion of the insulating layer under the waveguide core to form an air slot therein and to release the waveguide core such that the waveguide core is suspended over the air slot of the insulating layer by the second material layer, wherein a surface of the waveguide core is exposed to the air slot of the insulating layer.

10. The method according to claim 9, further comprising forming at least one through-hole in the second material layer to be in fluid communication with the portion of the insulating layer to be removed.

11. The method according to claim 9, wherein disposing a second material layer over the waveguide core comprises disposing the second material layer to cover a top surface and two opposing sidewall surfaces of the waveguide core.

12. The method according to claim 9, further comprising etching the insulating layer to form two trenches therein which are spaced apart, wherein disposing a second material layer over the waveguide core further comprises disposing the second material layer into the two trenches to form two sidewall portions which are spaced apart and constitute two opposing sidewalls of the air slot to be formed in said removing a portion of the insulating layer.

13. The method according to claim 9, wherein the waveguide core is shaped in the form of a strip.

14. The method according to claim 9, wherein the first material layer is a silicon layer.

15. The method according to claim 9, wherein the second material layer is a dielectric thin film layer.

16. The method according to claim 15, wherein the dielectric thin film layer includes a material selected from a group consisting of aluminum oxide, silicon nitride, germanium, and silicon.

17. An optical gas sensor comprising:
   a light source configured to emit light;
   a gas sensing section comprising an optical waveguide structure, the optical waveguide structure being arranged to receive the light from the light source and transmit the light received through the optical waveguide structure; and
   a light detector arranged to receive the light transmitted from the optical waveguide structure and configured to detect a gas in the gas sensing section based on the light received, wherein the optical waveguide structure comprises:
   a substrate;
   an insulating layer disposed on the substrate, the insulating layer comprising an air slot formed therein;
   a first material layer suspended over the air slot of the insulating layer, the first material layer constituting a waveguide core of the optical waveguide structure; and
   a second material layer disposed over the waveguide core, wherein the waveguide core is suspended over the air slot of the insulating layer by the second material layer.

18. The optical gas sensor according to claim 17, further comprising a tunable filter configured to receive the light from the light source and selectively transmit the light having a predetermined wavelength to the optical waveguide structure.

19. The optical gas sensor according to claim 17, wherein the optical gas sensor further comprises a cap wafer for enclosing a side of the optical gas sensor on which the gas sensing section is disposed to form a chamber therein, the cap wafer comprising one or more apertures in fluid communication with the chamber.

20. A method of fabricating an optical gas sensor, the method comprising:
   disposing a light source on a substrate, the light source configured to emit light;
   forming a gas sensing section on the substrate, the gas sensing section comprising an optical waveguide structure, the optical waveguide structure being arranged to receive the light from the light source and transmit the light received through the optical waveguide structure; and
   disposing a light detector on the substrate, the light detector arranged to receive the light transmitted from the optical waveguide structure and configured to detect a gas in the gas sensing section based on the light received, wherein the optical waveguide structure comprises:
   a substrate;
   an insulating layer disposed on the substrate, the insulating layer comprising an air slot formed therein;
   a first material layer suspended over the air slot of the insulating layer, the first material layer constituting a waveguide core of the optical waveguide structure; and
   a second material layer disposed over the waveguide core, wherein the waveguide core is suspended over the air slot of the insulating layer by the second material layer.

* * * * *